Feb. 16, 1960 D. H. MOREY, JR Plant Pat. 1,907
ROSE PLANT
Filed May 25, 1959
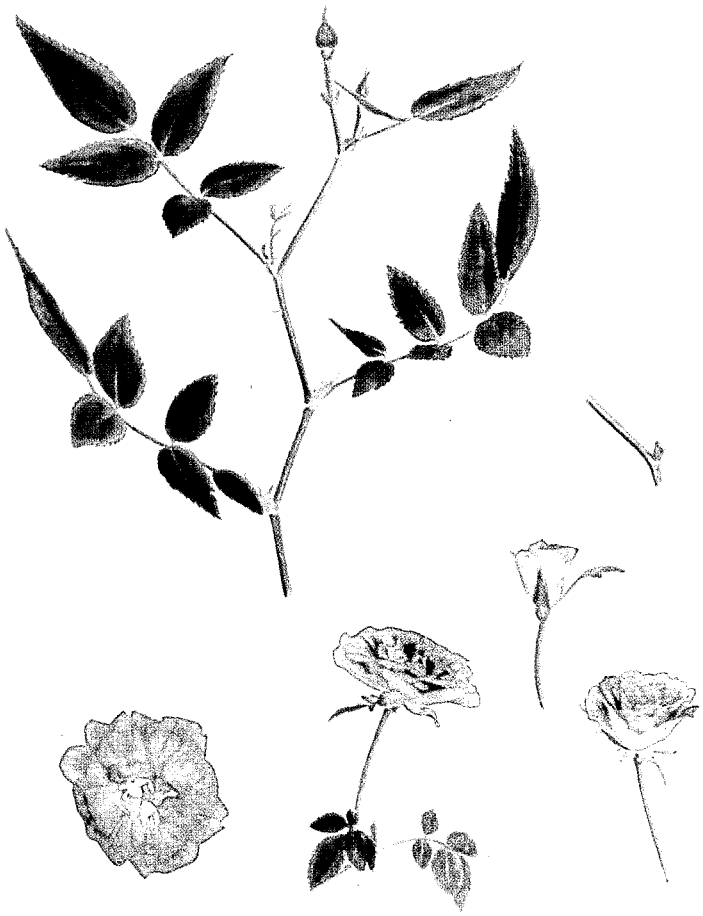
Inventor.
D. H. Morey, Jr.
By: Robb & Robb
Attorneys.

United States Patent Office

Plant Pat. 1,907
Patented Feb. 16, 1960

1,907

ROSE PLANT

Dennison H. Morey, Jr., Pleasanton, Calif., assignor to Jackson & Perkins Company, Newark, N.Y., a corporation of New York Application May 25, 1959, Serial No. 815,760

1 Claim. (Cl. 47—61)

The present invention relates to a new and distinct variety of rose plant of the miniature class, which was originated by me by crossing an unnamed and unpatented sport of "Dick Koster" (unpatented) with the variety "Tom Thumb" (Plant Patent No. 169), said latter variety also being known in Europe as "Peon."

The primary objective of this breeding was to produce a new rose variety characterized by a low-growing plant habit, and a habit of bearing flowers of miniature size. This objective was fully achieved, along with other desirable improvements, as evidenced by the following unique combination of characteristics which are outstanding in the new variety and which distinguish it from its parents, as well as from all other varieties of which I am aware:

(1) A miniature plant habit, averaging from 6 to 8 inches tall;

(2) A miniature flower size, averaging about ½" in diameter;

(3) An open, flat and double form of the flowers; and (4) A distinctive Carmine, lightly overcast with Spectrum Red, general color tonality of the flowers which is unusual and different from any other miniature rose.

Asexual reproduction of the new variety by own-rooted cuttings, as performed at Pleasanton, California, and also at Newark, New York shows that the aforementioned characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of the new variety, with color terminology in accordance with Ridgway's Color Standards and Nomenclature:

Parentage: Seedling.
*Seed parent.*—An unnamed sport of "Dick Koster."
*Pollen parent.*—"Tom Thumb."

Classification:
*Botanic.*—Hybrid chinensis minima.
*Commercial.*—Miniature.

*Flower*

(Observations made from specimens grown in a greenhouse at Newark, New York near mid-morning during the middle of December.)

Blooming habit: Recurrent—continuous.

Bud:
*Size.*—Small.
*Form.*—Ovoid; is not affected by wet or hot weather.
*Color.*—When sepals first divide—Tyrian Rose, Plate 12, lightly overcast with Amaranth Purple, Plate 12. When petals begin to unfurl—Spinel Red, Plate 12. When half-blown: inside of petals—Carmine, Plate 1, lightly overcast with Spectrum Red, Plate 1; reverse of petals—Tyrian Rose, Plate 12, lightly overcast with Amaranth Purple, Plate 12.
*Sepals.*—Branched; curl back when petals begin to unfurl. Color: inside—Pale Fluorite Green, Plate 32; outside—Light Hellebore Green, Plate 17.
*Calyx.*—Color—Biscay Green, Plate 17. Shape—pear. Size—small. Aspect—smooth. Odor when rubbed—none.
*Peduncle.*—Length—short. Aspect—smooth. Strength—erect; slender. Color—Oil Green, Plate 5.
*Opening.*—Opens up well; is not affected by adverse weather conditions.

Bloom:
*Size.*—Small. Average size when fully expanded—½ inch.
*Borne.*—Several together, and in irregular clusters.
*Stems.*—Short; normal strength.
*Form (when first open).*—Open. Permanence—flattens; outer petals curl back.
*Petalage.*—Double (full but open center). Number of petals under normal conditions—from 35 to 40.
*Color.*—Center of flower—Carmine, Plate 1. Outer petals—Carmine, Plate 1, lightly overcast with Amaranth Purple, Plate 12. Base of petal (aiglet)—Marguerite Yellow, Plate 30. Inside of petals—Carmine, Plate 1, lightly overcast with Spectrum Red, Plate 1. Reverse of petals—Spinel Red, Plate 26. General tonality from a distance—Carmine, Plate 1, lightly overcast with Spectrum Red, Plate 1.
*Discoloration.*—General tonality at end of first day—Carmine, Plate 1, lightly overcast with Spectrum Red, Plate 1. Second day—Carmine, Plate 1, lightly overcast with Spectrum Red, Plate 1. Third day—Carmine, Plate 1, lightly overcast with Amaranth Purple, Plate 12.

Petals:
*Texture.*—Thin; is not affected by wet or hot weather.
*Appearance.*—Inside—satiny. Outside—shiny.
*Form.*—Oval.
*Arrangement.*—Imbricated (regularly arranged shingle-like).
*Petaloids in center.*—Few; small.
*Persistence.*—Drop off cleanly.
*Fragrance.*—Moderate. Nature—tea (average hybrid tea scent).
*Lasting quality.*—On the plant—long. As cut flower—long.

*Genital organs*

Stamens, anthers: Small; few; regularly arranged around styles. Color—Pinard Yellow, Plate 4.
Stamens, filaments (threads): Short. Color—Martius Yellow, Plate 4.
Pollen: Color—Maize Yellow, Plate 4.
Styles: Loosely separated; uneven length; short; thin.
Stigmas: Color—White, Plate 53.
Ovaries: All enclosed in calyx.
Hips: None.
Seeds: None.

*Plant*

Form: Bush; from 6 inches to 8 inches tall.
Growth: Medium; dwarf; compact.
Foliage: Compound of 5 to 7 leaflets.
*Size.*—Small.
*Quantity.*—Normal.
*Color.*—New foliage: upper side—Forest Green, Plate 17; under side—Light Bice Green, Plate 17. Old foliage: upper side—Cress Green, Plate 31; under side—Light Cress Green, Plate 31.

*Shape.*—Oval pointed.

*Texture.*—Upper side—glossy. Under side—smooth.

*Ribs and veins.*—Light.

*Edge.*—Serrated (saw toothed).

*Serration.*—Double; small.

*Leaf stem.*—Color—Absinthe Green, Plate 31. Under side—prickly.

*Stipules.*—Short; bearded.

Wood:

*New wood.*—Color—Spinach Green, Plate 5. Bark—smooth.

*Old wood.*—Color—Cerro Green, Plate 5. Bark—smooth.

Thorns:

*Thorns.*—Quantity: on main stalks from base—few; on laterals from stalk—few. Form—narrow base; short. Color (when young)—Chatenay Pink, Plate 13. Position—irregular.

*Prickles.*—Quantity: on main stalks—none; on on laterals—none.

*Short needles.*—Quantity: on main stalks—none; on laterals—none.

I claim:

A new and distinct variety of rose plant of the miniature class, substantially as herein shown and described, characterized particularly as to novelty by the unique combination of a miniature plant and flower size, an open, flat and double form of the flowers, and a distinctive Carmine, lightly overcast with Spectrum Red general color tonality of the flowers.

No references cited.